United States Patent [19]

Sasaki et al.

[11] Patent Number: 5,470,707
[45] Date of Patent: Nov. 28, 1995

[54] HYDROGEN BOND LABELING AND BASE SEQUENCE DETERMINATION METHODS FOR DNA OR RNA

[75] Inventors: Yuji Sasaki, Kawagoe; Yoshinori Harada, Hatoyama, both of Japan

[73] Assignee: Hitachi, Ltd., Tokyo, Japan

[21] Appl. No.: 25,997

[22] Filed: Mar. 4, 1993

[30] Foreign Application Priority Data

Mar. 4, 1992 [JP] Japan .................................. 4-046687

[51] Int. Cl.$^6$ .............................. C12Q 1/68; C07H 21/00
[52] U.S. Cl. ............................................. 435/6; 536/25.32
[58] Field of Search ............................... 435/6; 536/25.32

[56] References Cited

U.S. PATENT DOCUMENTS 5,106,729  4/1992  Lindsay et al. ............................. 435/6

OTHER PUBLICATIONS

S. L. Commerford, Biochemistry, "Iodination of Nucleic Acids in Vitro", vol. 10, No. 11, pp. 1993–1999 (1971).
Matthews, J. A., et al. Review: Analytical Strategies for the Use of DNA Probes, Anal. Biochem. (1988) 169:1–25.
UK Patent GB2235049, published Feb. 20, 1991, Scanning microscopes for chemical bond microscopy. (Abstract).

Primary Examiner—Margaret Parr
Assistant Examiner—David Schreiber
Attorney, Agent, or Firm—Fay, Sharpe, Beall, Fagan, Minnich & McKee

[57] ABSTRACT

A hydrogen bond labeling and base sequence determination method for DNA or RNA takes advantage of the complementary nature of the fundamental structure of DNA or RNA bases to bind corresponding chemical species with the base species of a denatured DNA or RNA chain. After providing an aqueous solution containing a nucleic acid, heating the aqueous solution to cleave the nucleic acid; cooling the aqueous solution and adding a base-specific labeling molecule having available hydrogen bonds to the aqueous solution, the base-specific labeling molecules bond to the available bases in a one-to-one fashion via the available hydrogen bonds. The resulting labeled molecule can be microscopically observed to determine the base sequence of the nucleic acid.

17 Claims, 3 Drawing Sheets

```
┌A―TPPP          ┌T┐
├G―CPP           │PG―C┤
├T               │PPPT―A┤
├C―GP            │PPC―G┤
├T               │PPPT―A┤
└T               └PPPT―A┘
```
FIG.1(c)   FIG.1(d)
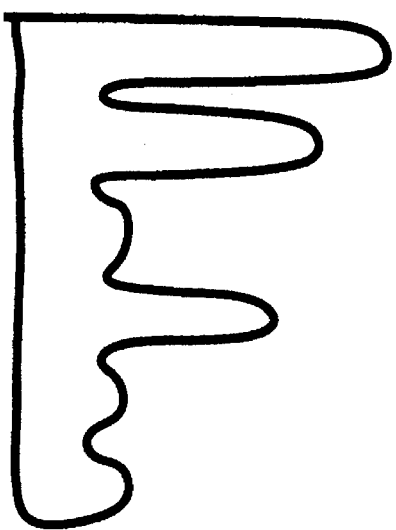
FIG.2(a)
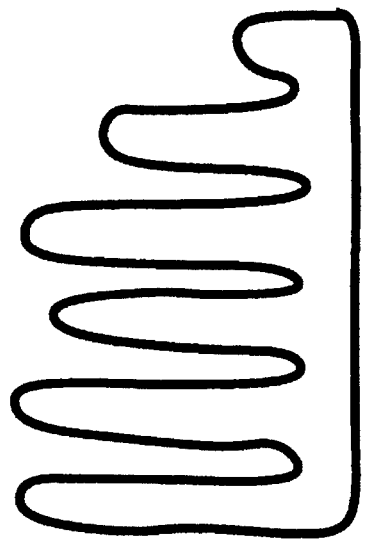
FIG.2(b)

HYDROGEN BOND LABELING AND BASE SEQUENCE DETERMINATION METHODS FOR DNA OR RNA

BACKGROUND OF THE INVENTION

1. Field of the Invention

The present invention relates to a nondestructive labeling method and a base sequence determination method for DNA or RNA.

2. Description of the Related Art

Among the known methods for analyzing DNA or RNA are the electrophoretic base sequence determination methods, such as the Maxam-Gilbert method and the dideoxy method. Even when the most sensitive radioisotope is employed as a detecting means in these methods, however, each trial run requires at least 1 pmol of the DNA or RNA. In addition, each of these methods involves a complicated preparation and determination procedure that requires several hours or longer for analysis. Accordingly, these methods are unsuitable for determining the base sequence of a DNA or RNA molecule having a large number of bases (for example, the entire human DNA or RNA chain).

In addition to the radioisotope and fluorescence methods, a method known as the heavy atom labeling method has been employed. See, for example, S. L. Commerford, *Biochemistry*, Vol. 10, page 1993 (1971). This method, however, does not aim to specifically label a particular individual base, and therefore has not been developed as a base sequence determination method. Furthermore, a transmission electron microscope is required for the heavy atom labeling method, making it difficult to directly observe the labeled sample in or out of an aqueous solution.

Another method is described in Japanese Kokai No. 3-198798. A base sequence determination method for nucleic acids is disclosed that uses a scanning tunneling microscope (STM) or an atomic force microscope (AFM), depending upon a difference in electrical conductivity. However, base-specific labeling is not employed in this method.

SUMMARY OF THE INVENTION

The present invention aims to provide a nondestructive labeling method using a simple procedure of hydrogen bond labeling (HBL), wherein the characteristics of nucleic acids are utilized to determine the base sequence of a DNA or RNA molecule.

In accordance with the present invention, a hydrogen bond labeling method takes advantage of the complementary nature of the fundamental nucleic acid base structure by adding base-specific labeling molecules to a denatured aqueous solution containing a nucleic acid. The base-specific labeling molecules bond to the available bases in a one-to-one fashion via hydrogen bonds, resulting in a labeled nucleic acid molecule whose base sequence can be determined by microscopically observing the labeled molecules.

BRIEF DESCRIPTION OF THE DRAWINGS

FIG. 1(a) illustrates a portion of a DNA molecule prior to denaturation;

FIG. 1(b) illustrates the DNA molecule following denaturation;

FIG. 1(c) shows one side of the DNA molecule after labeling in accordance with the invention;

FIG. 1(d) shows the other half of the denatured DNA molecule following a labeling step in accordance with the teachings of the present invention;

FIGS. 2(a) and (b) show schematically an STM measurement result of the labeled DNA halves of FIGS. 1(c) and 1(d), respectively;

DETAILED DESCRIPTION OF THE PREFERRED EMBODIMENTS

Figure 3:
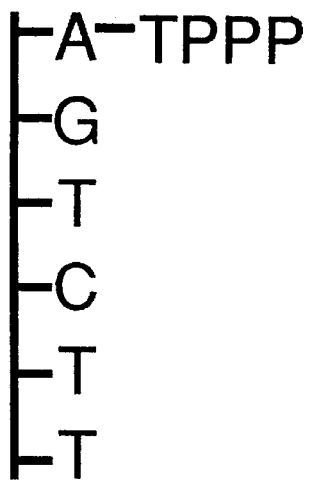
FIG. 3 shows the applicability of the present invention to confirming the location of a single base species.

In accordance with the present invention, a hydrogen bond labeling method takes advantage of the complementary nature of the fundamental structure of the DNA or RNA bases. In a double-stranded DNA chain, for example, adenine A, one of the base species, binds to thymine T, while guanine G binds to cytosine C by hydrogen bonds in each case.

In further accordance with the present invention, a DNA sample (for example) is heated to disconnect the A-T bond (denaturation), and then a chemical species containing the chemical group of thymine T, for example thymidine triphosphate (TTP), is added in an excessive amount to the solution during a slow cooling (renaturation) process during which the bases of the DNA molecules can again form bonds. Thus, instead of the original A-T bond, a new A-TTP bond is formed at each free adenine base. As a result, the DNA strand, once denatured, does not revert to the original double strand.

Similarly, the other bases can be labeled using molecules capable of specifically binding to the other bases. For example, deoxyadenosine diphosphate (dADP), deoxycytidine monophosphate (dCMP), and deoxyguanosine diphosphate (dGDP) can be added in an excessive amount to bond with the T, G and C bases, respectively. In order to determine the base sequence, though, three labeling species suffice, with the fourth, unlabeled base being determinable as the only unlabeled base.

Then, the labeling molecules having been chosen so that the labeled DNA bases have different contours when observed using a scanning tunneling microscope (STM), the base sequence can be determined for the entire molecule by observing the labeled molecules. One example of a distinguishing characteristic that is observed under the STM (or atomic force microscope (AFM) or scanning electron microscope (SEM)) is the length of the labeled DNA base on the hydrogen bond side. Thus, for the specific examples of labeling molecules mentioned above, thymidine triphosphate is longer than deoxyadenosine diphosphate, which in turn is longer than deoxycytidine monophosphate. Bases labeled with each of these three phosphate labels are longer than the unlabeled cytosine base. Therefore, when viewed using the STM, the individual bases can be distinguished on the basis of molecular length, and the base sequence can be accordingly determined.

The labeling molecules are not particularly restricted so long as each carries a chemical species capable of binding to adenine, cytosine, guanine or thymine via stable hydrogen bonds, has side chains differing in some fashion under an STM or other means of microscopic observation, and each labeling molecule has a size which does not cause any steric hindrance in the labeling of the adjacent base. The preferred labeling criterion is the length of the labeling molecule, mentioned above. Further examples of useful labeling molecules include those capable of being discerned by the spatial resolving power of the observation means (for example, coenzymes having a nucleotide-like structure and synthetic molecules satisfying the requirements described above).

An additional requirement for the labeling molecule is that it not suffer from breakage or partial cleavage of the bonds upon heating, since the denatured nucleic acid solution will be cooling from a temperature of approximately 90° C.

In accordance with the teachings of the present invention, a double-stranded DNA molecule can also be labeled. In this case, a Hoogsteen-type hydrogen bond is newly formed and, as a result, a hydrogen triple-stranded DNA molecule results.

In addition to advancing the art on the basis of the single-molecule resolution, the HBL method, being a direct observation method, requires only 1 fmol or less of a sample. Thus, the amount of sample required is extremely small compared with the existing base sequence determination methods.

To further illustrate the present invention, the following example is offered.

Figures 1A, 1B:
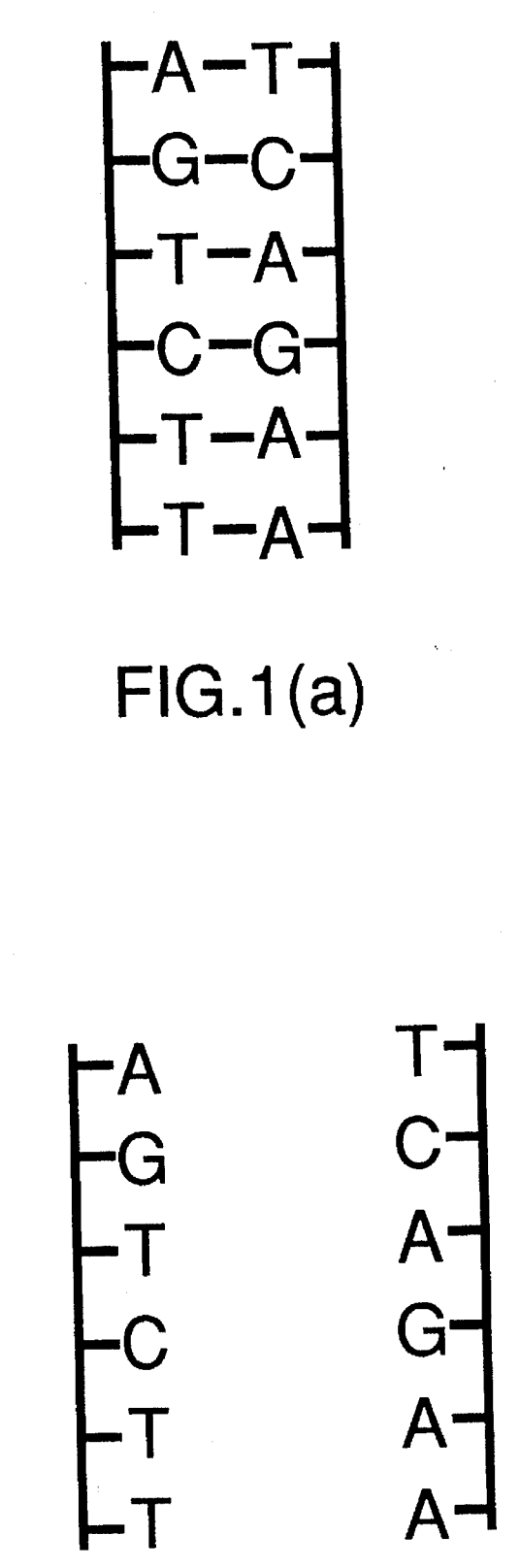

A DNA molecule (FIG. 1(a)) was prepared by cleaving ΦX174 (5386 base pairs (bp)) with a restriction enzyme HincII, and purifying a fragment of 79 bp thus obtained to a concentration of 0.1 nmol/ml (pH 7.0). Ten μl of an aqueous solution containing 1 pmol of the DNA was heated to about 90° C. to thereby modify, or denature, the DNA (FIG. 1(b)). Next, the aqueous solution was slowly cooled to room temperature.

During the cooling process, when the solution reached approximately 75° C., deoxyadenosine triphosphate (dATP), deoxyguanosine diphosphate (dGDP) and deoxycytidine monophosphate (dCMP), each previously heated, were added to the solution in an amount equimolar with the DNA, or larger by a factor of ten.

Then, after being cooled to room temperature, the denatured DNA solution was deposited on a graphite substrate, or gold film (about 200 nm) evaporated onto mica, using a 1.5 μl (corresponding to 150 fmol/ml) micropipette, followed by drying under reduced pressure. The amount of the sample is not limitative in the base sequence determination method of the present invention. In principle, the base sequence determination method of the present invention can be performed by using only a single strand of DNA. The concentration given above, however, allows the labeled DNA to be adsorbed in a thickness of nearly one layer per square centimeter, enabling efficient observation.

In this example, the base length was adjusted to 79 bp, because it was desired to observe the entire DNA in a visual field of about 30 nm×30 nm, and to promote the two-dimensional development of the denatured DNA by minimizing the formation of any higher ordered structure in the single-stranded DNA, such as the formation of a hair-pin loop. Theoretically, the HBL treatment can be utilized on considerably longer bases.

Next, the contour, or external form, of the sample was observed under a scanning tunneling microscope (STM), FIG. 1(c) is a schematic view obtained by the observation.

As shown, the detailed structures of the base moieties of the adenine A, cytosine C and guanine G contained in the labeled molecules (i.e., deoxyadenosine triphosphate (dATP), deoxyguanosine diphosphate (dGDP) and deoxycytidine monophosphate (dCMP)) cannot be distinguished from each other, but the phosphate group moieties connected to these base moieties clearly differ from each other in length. Thus, the DNA base complementarity by which each labeling molecule can be identified makes it possible to directly determine the DNA base sequence. FIG. 1(d) shows the state of the labeled single-stranded DNA chain which is complementary with the above-mentioned single-stranded DNA shown in FIG. 1(c).

FIGS. 2(a) and 2(b) illustrate how the labeling molecules corresponding to the bases constituting the DNA molecule differ from each other in length, so that each base can be easily identified by its label. FIGS. 2(a) and 2(b) are representations of STM images, but illustrate how any other microscopic observation technique would indicate the base sequence.

Observation using the SEM can be effected using a low-speed accelerating voltage (about 1 keV) to give a clear contrast to the base plate. To achieve a clearer contrast still, the sample can be coated with a metal such as platinum.

Observation under the STM or AFM under reduced pressure, or in air, does not cause any contamination of the surface of the sample. In addition, a DNA image can easily be obtained Using the STM or AFM. In particular, although a DNA chain of a film thickness of approximately 3 nm or above cannot be examined under the STM, a DNA of a film thickness of 3 nm or above can be observed under the AFM.

Of course, the foregoing example can be carried out using any combination of three labeled bases, or even by labeling all four bases.

FIG. 3 shows another example illustrating the teachings of the present invention. As shown in FIG. 3, the labeling molecule thymidine triphosphate (TTP) is bound exclusively to the adenine base A, via hydrogen bonds. Thus, the present invention is applicable to confirming the location of a single base species.

Recognition of the utility of the present invention for labeling a single base enables a base sequence to be determined by a related method. Thus, rather than labeling three different bases in a single labeling process, and observing the DNA chain under a microscope, successive labeling procedures can be carried out, each for a single base.

Figure 4:
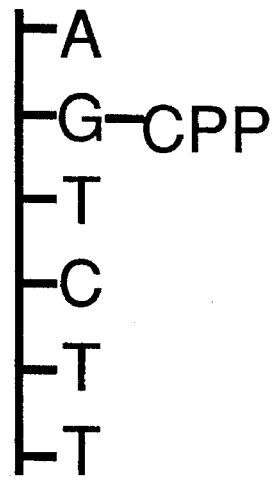
FIGS. 4 and 5 in conjunction with FIG. 3, show the individual labeling of three base species in accordance with a further embodiment of the invention in which an entire DNA chain can be labeled.
Figure 5:
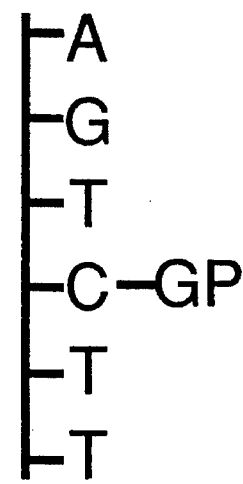
Figure 6:
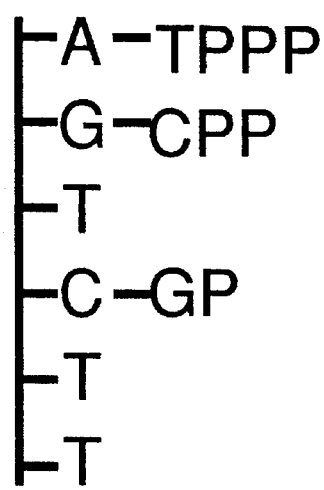
FIG. 6 shows a base sequence determined by combining the results of the labeled base species of FIGS. 3–5.

For example, following the labeling of base A by using TTP (thymidine triphosphate) as shown in FIG. 3, base G can be labeled using deoxycytidine diphosphate (dCDP), shown in FIG. 4. Thereafter, base C can be labeled using deoxyguanosine monophosphate (dGMP) as shown in FIG. 5. These labeling steps result in three individually-labeled chains of DNA. The data from all three labeling procedures can be processed to determine the base sequence for the DNA molecule as a whole (FIG. 6).

An advantage of this embodiment lies in the decreased statistical error associated with resolving one molecular form from an adjacent molecular form. For example, when three bases of a single DNA chain are labeled in a single process, as described in conjunction with the embodiment of FIGS. 1 and 2, adjacent molecules having similar lengths (for example) can be difficult to distinguish.

However, when only a single base species is to be labeled in a single process, the labeled base species stands out with greater particularity in comparison to the unlabeled bases. Known data processing methods can then combine the observed labeling results to obtain the base sequence with greater accuracy.

In FIGS. 3, 4 and 5, the labeling molecules are not particularly restricted to TTP, dCDP, and dGMP. For example, TTP, dCTP and dGTP which are observed to have about the same contour by using STM can label the bases A, G and C, respectively, according to this embodiment, because their respective contours need not be different to distinguish the labeled bases by this method.

Thus, according to the present invention, the base sequence of a DNA or RNA molecule can be determined without requiring cloning or amplification of genes, nor troublesome enzymatic treatments or analytical treatments. Thus, human genome analysis can be rapidly conducted, in comparison with existing methods.

Furthermore, since the hydrogen bonds are easily broken by heating, the present method is harmless to the DNA samples, and thus the samples can be reused after reversing the labeling process.

Various modifications of the invention as set forth in the foregoing description will become apparent to those of ordinary skill in the art. All such modifications that basically rely on the teachings through which the invention has advanced the state of the art are properly considered within the spirit and scope of the invention.

We claim:

1. A method for labeling a nucleic acid base of a DNA or RNA molecule, comprising the steps of:

preparing an aqueous solution containing a double-stranded DNA or RNA molecule;

heating the aqueous solution to denature the double-stranded DNA or RNA molecule so that the double strand dissociates into single strands having complementary nucleotide sequences;

adding at least one base-specific labeling molecule to the aqueous solution;

cooling the aqueous solution so that the base-specific labeling molecule is hybridized to complementary bases on the single strands to form a contour of each of the single strands defined by said at least one base-specific labeling molecule; and further cooling the aqueous solution so that the single strands, having the hybridized base-specific labeling molecule, are independently bound on a substrate; the contour of each of said independently bound strands, due to the hybridized base-specific labeling molecule, representing a base sequence thereof.

2. A method for determining a base sequence of a DNA or RNA molecule, comprising the steps of:

preparing an aqueous solution containing a double-stranded DNA or RNA molecule;

heating the aqueous solution to denature the double-stranded DNA or RNA molecule so that the double strand dissociates into single strands having complementary nucleotide sequences;

adding at least one base-specific labeling molecule to the aqueous solution;

cooling the aqueous solution so that the base-specific labeling molecule is hybridized to complementary bases on the single strands to form a contour of each of the single strands defined by said at least one base-specific labeling molecule;

further cooling the aqueous solution so that the single strands, having the hybridized base-specific labeling molecule, are independently bound on a substrate; the contour of each of said independently bound strands, due to the hybridized base-specific labeling molecule, representing a base sequence thereof; and microscopically determining the base sequence of the double-stranded DNA or RNA molecule from the contour of at least one of the bound strands.

3. A method for determining a base sequence as claimed in claim 2, wherein the microscopically determining step is performed by a scanning tunneling microscope.

4. A method for determining a base sequence as claimed in claim 2, wherein the microscopically determining step is performed by a scanning electron microscope.

5. A method for determining a base sequence as claimed in claim 2, wherein the microscopically determining step is performed by an atomic force microscope.

6. A method for determining a base sequence of a DNA or RNA molecule, comprising the steps of:

preparing first, second and third aqueous solutions containing identical double-stranded DNA or RNA molecules;

heating the first, second, and third aqueous solutions to denature the respective double-stranded DNA or RNA molecules so that each of the double strands dissociates into single strands having complementary nucleotide sequences;

adding at least one first, at least one second, and at least one third base-specific labeling molecule to the first, second, and third aqueous solutions, respectively;

cooling the first, second, and third aqueous solutions so that the respective base-specific labeling molecule added to each aqueous solution is hybridized to complementary bases on the single strands in the respective aqueous solution, to form a contour of each of the single strands defined respectively by said at least one first, at least one second, and at least one third base-specific labeling molecule;

further cooling the first, second, and third aqueous solutions so that each single strand, having the respective hybridized base-specific labeling molecule, is independently bound on a substrate; the contour of each of said independently bound strands, due to the respective hybridized base-specific labeling molecule, representing a base sequence thereof;

determining the labeled sequence of each of the independently bound single strands from the respective contours thereof; and determining the base sequence of the identical double stranded parts of DNA or RNA from the step of determining the labeled sequence of each of the independently bound single strands.

7. A method for determining a base sequence as claimed in claim 6, wherein the step of determining the labeled sequence is performed by a scanning tunneling microscope.

8. A method for determining a base sequence as claimed in claim 6, wherein the step of determining the labeled sequence is performed by a scanning electron microscope.

9. A method for determining a base sequence as claimed in claim 6, wherein the step of determining the labeled sequence is performed by an atomic force microscope.

10. A method for determining the location of a single base species of a DNA or RNA molecule, comprising the steps of:

preparing an aqueous solution containing a double-stranded DNA or RNA molecule;

heating the aqueous solution to denature the double-stranded DNA or RNA molecule so that the double strand dissociates into single strands having complementary nucleotide sequences;

adding at least one base-specific labeling molecule to the aqueous solution;

cooling the aqueous solution so that the base-specific labeling molecule is hybridized to complementary bases on the single strands to form a contour of each of the single strands defined by said at least one base-specific labeling molecule;

further cooling the aqueous solution so that the single strands, having the hybridized base-specific labeling molecule, are independently bound on a substrate; the contour of each of said independently bound strands, due to the hybridized base-specific labeling molecule, representing a base sequence thereof; and microscopically determining the labeled base of the double-stranded DNA or RNA molecule from the contour of at least one of the bound strands.

11. A method for determining the location of a single base species as claimed in claim 10, wherein the microscopically determining step is performed by a scanning tunneling microscope.

12. A method for determining the location of a single base species as claimed in claim 10, wherein the microscopically determining step is performed by a scanning electron microscope.

13. A method for determining the location of a single base species as claimed in claim 10, wherein the microscopically determining step is performed by an atomic force microscope.

14. A method for labeling a nucleic acid base as claimed in claim 1, wherein the adding step is performed during the cooling step.

15. A method for determining a base sequence as claimed in claim 2, wherein the adding step is performed during the cooling step.

16. A method for determining a base sequence as claimed in claim 6, wherein the adding step is performed during the cooling step.

17. A method for determining the location of a single base species as claimed in claim 10, wherein the adding step is performed during the cooling step.

* * * * *